April 2, 1963 G. J. VON ABRAMS Plant Pat. 2,244
ROSE PLANT
Filed Oct. 23, 1961
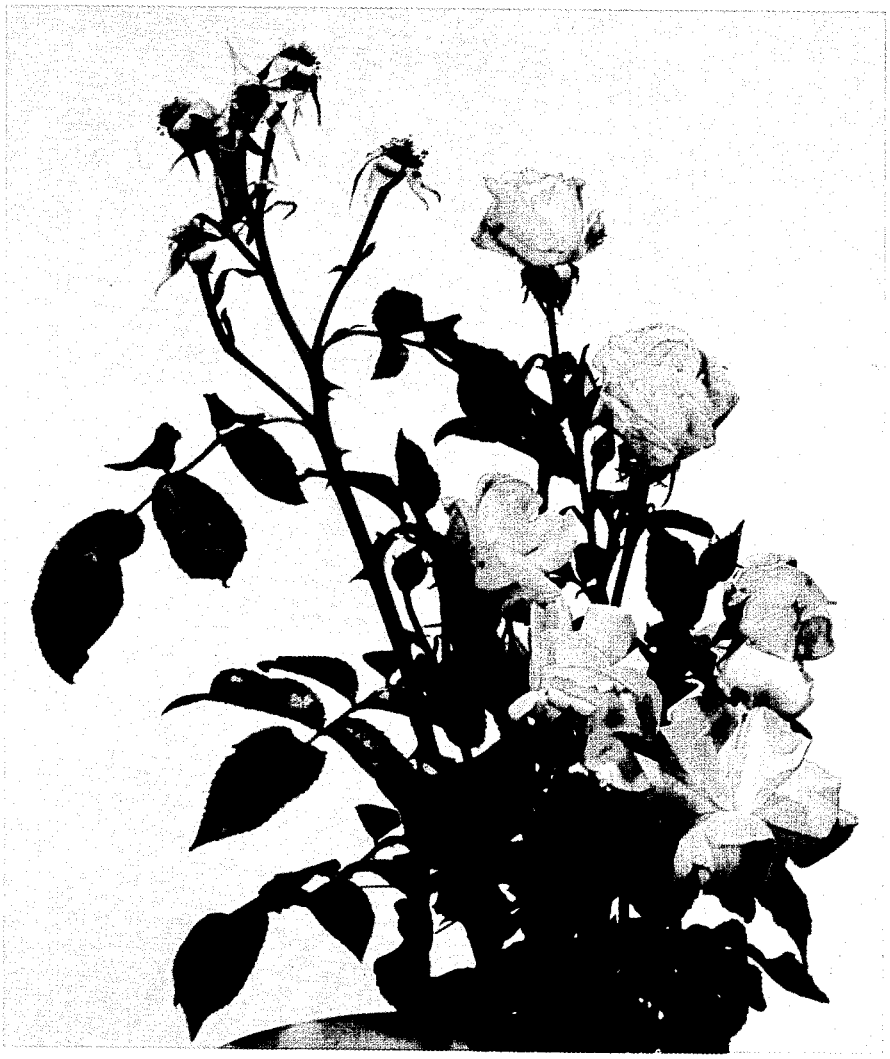
INVENTOR.
GORDON J. VON ABRAMS
BY T. R. Geisler.
ATTORNEY United States Patent Office Plant Pat. 2,244
Patented Apr. 2, 1963

2,244
ROSE PLANT

Gordon J. Von Abrams, 3463 NW. Savier St.,
Portland, Oreg.

Filed Oct. 23, 1961, Ser. No. 147,112
1 Claim. (Cl. 47—61)

This invention comprises a new and distinct variety of rose plant of the commercial "floribunda" class which was obtained by pollinating the rose variety "Goldilocks" (Plant Patent No. 672) with pollen of the rose variety "P.D. No. 51121-1" (not in commerce).

The objectives of this particular breeding were to produce a rose plant having flowers of unique multicolor pigmentation in the orange-red and yellow range, as well as a rose plant having plant and habit characteristics appropriate for a rose plant of the floribunda class. These objectives were successfully achieved.

The pollination took place at Scappoose, Oregon, in June 1952. The first asexual propagation was performed in July 1954, at Scappoose, Oregon, by bud-grafting, and the new plant has retained its distinguishing characteristics through successive propagations by bud-grafting.

This new rose plant is a seeding, medium-low bush type, suitable for use outdoors either for garden decoration or for cut flowers. Its main distinctive feature is the unique flower color and this feature alone, and in combination with the other characteristics as herein described, make this new variety readily distinguishable from other varieties known to me in commerce. In general, the petals of the newly opened flower give the impression of a blending from yellow to red on both inside and outside surfaces, predominantly yellow on the outside surface, predominantly orange-red on the inside surface, but a more correct and detailed description of the unique coloring is given below. The plant blooms abundantly outdoors, blooming almost continuously during the growing season.

The accompanying illustration shows the vegetative growth and the flowers of this new rose plant in different stages of development, the colors in the illustration showing the actual colors as nearly as is reasonably possible in a color reproduction of this type.

In the following detailed description the following color references are used:

(1) Wilson, R. F.; Royal Horticultural Society Colour Chart, England, 1940 (hereinafter abbreviated "W").

(2) Ridgway, R.; Color Standards and Color Nomenclature, Washington, D.C., 1912 (hereinafter abbreviated "R").

*Flowers*

The flowers are borne many per stem, in moderately compact, irregular to rounded cymose clusters, on normal, medium length stems. The flower longevity is short. The flowers have a moderate fragrance.

Flower color: The following description of newly opened flowers was made in August 1960, from specimens grown outdoors near Scappoose, Oregon.

*Outside petal.*—Outer surface—base near Aureolin (W. 3/1 to 3/2, p. 3) blending gradually upward to near Saturin Red (W. 13/3, p. 13), predominant color near Aureolin (W. 3/2, p. 3). Inner surface —base near Aureolin (W. 3, p. 3), blending abruptly above into near Saturn Red (W. 13 to 13/1, p. 13), which is the predominant color.

*Intermediate petal.*—As above.

*Inside petal.*—As above.

*General color effect.*—Saturn Red (W. 13, p. 13) with distinct center near Aureolin (W. 3, p. 3).

The following description of mature flowers was made in August 1960, from flowers which had been open for three days on a plant grown outdoors near Scappoose, Oregon.

*Outside petal.*—Outer surface—base near Sulphur Yellow (W. 1/2 to 1/3, p. 1) blending gradually upward to near Saturn Red (W. 13/3, p. 13), predominant color near Sulphur Yellow (W. 1/3, p. 1). Inner surface—a small spot of Sulphur Yellow (W. 1/1, p. 1) at the extreme tip of the base, fading upward to Sulphur Yellow (W. 1/3, p. 1), then flushing upward rather abruptly into near Mandarin Red (W. 17/2, p. 17) or near Vermillion (W. 18/2, p. 18).

*Intermediate petal.*—As outside petal.

*Inside petal.*—As outside petal.

*General color effect.*—Near Mandarin Red (W. 17/2, p. 17) with center near Sulphur Yellow (W. 1/3, p. 1).

Behavior in senescence:

Color—in general, as the flower ages, the yellow pigments fade, and the anthocyanin pigments become more blue. The center of the flower fades to nearly white. On the inner surface, the orange color fades and blues gradually to near Scarlet (W. 19/3, p. 19) or Begonia (W. 619/2 to 619/3, p. 146). Toward the apex, irregular spots or markings may appear, i.e., near Geranium Lake (W. 20, p. 20) or even darker. Petals drop cleanly under nearly all weather conditions.

Open Flower:

*Size.*—Small (i.e.—9 cm.).

*Petalage.*—Semi-double (ca. 18 to 25).

*Form.*—High-centered at first, later becoming open. Petals cupped outward. Usually 3 or 4 irregular petals at center.

Petals:

*Substance.*—Medium thicknes; firm; flexible.

*Texture.*—Outside shiny; inside satiny.

*Shape and size (in open flower).*—Outside petal—obovate; i.e.—4 x 4 cm.; apex irregularly notched. Intermediate petal—obovate; i.e.—4 cm. wide by 4.5 cm. long; apex mucronate. Inside petal—usually 3 or 4 irregular petals.

Bud:

*Pedicel.*—Size—medium (i.e.—ca. 2 mm. x 2 to 4 cm.). Strength—erect. Color—near Scheele's Green (R. 33. GY-G. *i*, Plate VI); usually with one side flushed red. Surface—smooth except for numerous gland-tipped reddish cilia.

*Sepals.*—Size—small (i.e.—8 x 22 mm.). Form—spear-shaped. Point—medium size; aristate; margins near-entire. Lateral margins—numerous glandular cilia; bristle-like appendages, none to 3 or more.

*Surface.*—Outer—glossy, glandular; slight, near-white, fine pubescence. Inner—tomentose.

*Color.*—Outer surface—near Scheele's Green (R. 33. GY-G. *i*, Plate VI) often flushed reddish. Inner surface—near Clear Fluorite Green (R. 33". GY-G. *b*, Plate XXXII). Behavior—reflex.

*Before calyx breaks.*—Size—small (i.e.—2.2 x 1.1 cm.). Form—long pointed, with medium bristly terminal points. Surface—with several bristly appendages; several gland-tipped cilia.

*As calyx breaks.*—Exposed petal color near Poppy Red (W. 16, p. 16).

*As first petal opens.*—Size of bud—small (i.e.—3 cm. long). Form of bud—medium pointed. Color—outer surface—base near Aureolin (W. 3/1, p. 3) flushed upward to near Indian Yellow (W. 6/2, p. 6) irregularly flushed with Poppy Red (W. 16 to 16/2, p. 16); inner surface—base near Aureolin (W. 3, p. 3) merging shortly above with the predominant color, near Fire Red (W. 15 to 15/1, p. 15).

*Opening habit.*—Opens regularly in nearly all weather conditions.

*Plant*

Foliage:

*Leaves.*—Compound of usually 5, often 7, leaflets. Abundant. Size—small to medium.

*Leaflets.*—Substance—medium thick; hard; flexible. Texture—smooth; glossy.

*Size.*—Small to medium (i.e.—2.5 x 4.5 cm. to 3.5 x 6.5 cm.).

*Shape.*—Ovate. Base rounded; tip acute. Margin singly serrate.

*Color.*—Mature: upper surface—related to, but darker than Spinach Green (W. 0960, p. 187); under surface—near Light Hellebore Green (R. 25′. YG-Y. *k,* Plate XVII). Young: upper surface—near Maroon (R. 3. O-R. *m,* Plate 1); under surface—near Dark Indian Red (R. 3″ O.R. *m,* Plate XXVII).

*Rachis.*—Caliber—medium. Upper side—ridges thin, with few glandular cilia; groove slightly pubescent at basal end. Under side—few thorns; several glandular cilia.

*Stipules.*—Size—medium, long and slender (i.e.—6 x 15 mm.) but sometimes (on old leaves) as large as 8 x 30 mm. Points—medium; slightly curved; turned out at an angle usually greater than 45°. Margins—glandular.

*Disease resistance.*—Ordinary.

Growth:

*Habit.*—Low-growing, compact, well-branched, symmetrical.

*Vigor.*—Free.

*Canes (in second year of growth).*—Caliber—small to medium. Surface—rough, mostly corky; with few to several small, slender brown thorns. Color—near Grass Green (R. 33. GY-G. *k,* Plate VI) largely to near-completely overlain with brown and tan corky tissue.

*Main stems (of current year's growth).*—Caliber—small. Surface—moderately smooth, but with large rough corky areas; thorns—several to numerous; medium small (i.e.—6 mm. long); hooked downward; base generally short, oval; color brown. Color—near Spinach Green (W. 0960/1, p. 187) with dark brown to light tan corky areas.

*Branches (currently bearing senescent flowers).*—Caliber—small. Surface—moderately smooth, but with many small lenticels; thorns—several; small to medium; nearly straight to hooked slightly downward; base usually short oval (i.e.—3 mm. wide x 5 mm. long); color near, but lighter than, Liver Brown (R. 7′. R-O. *m,* Plate XIV). Color— between Spinach Green (R. 29. GG-Y. *m,* Plate V) and Lettuce Green (R. 29. GG-Y. *k,* Plate V), generally flushed unilaterally near Dark Livid Brown (R. 1‴. Red. *k,* Plate XXXIX).

*New shoots (in rapid growth).*—Surface—moderately smooth, with many small lenticels; thorns—several; medium size; nearly straight to hooked slightly downward, base oval; color near Bordeaux (R. 71. V-RR. *k,* Plate XII). Color—near Dark Indian Red (R. 3″. O-R. *m,* Plate XXVII), with varying green areas showing through the dominant red color.

Low-temperature tolerance: Ordinary for class.

*Reproductive Organs*

Stamens:

*Quantity.*—Moderate.

*Position.*—Immediately within corolla, at base of the calyx tube disc.

*Filaments.*—Medium length (i.e.—ca. 6–9 mm.); color yellow; all or nearly all with functional anthers.

*Anthers.*—Small; light orange.

*Pollen.*—Abundant; viable; deep yellow.

Pistils:

*Quantity.*—Moderate (i.e.—ca. 40).

*Styles.*—Medium length (i.e.—8 mm. above disc); free, but in small compact column; normal contortion.

*Stigmas.*—Small; light greyish yellow.

*Ovaries.*—Enclosed.

Receptacle and calyx tube:

*Size.*—Small (i.e.—8 mm. high and 6 mm. diameter).

*Shape.*—Obovate.

*Disc.*—Very prominent, high rounded. The prominence of the disc is accentuated by the unusually wide separation between filaments and styles, the latter being restricted to a narrow orifice.

*Surface.*—Fine, near white pubescence—not conspicuous. Somewhat glaucous.

*Color.*—Near Biscay Green (R. 27′. G-Y. *i,* Plate XVII).

Fruit (seed-pod):

*Quantity.*—Few to moderate.

*Size.*—Small.

*Shape.*—Globose.

*Sepals.*—Persist.

*Surface.*—Smooth.

*Wall.*—Medium thick, fleshy.

*Color.*—Orange, variable.

Seeds: Quantity ordinary; size small; viability good.

Having thus disclosed my invention, I claim:

A new and distinct variety of rose plant of the "floribunda" class, substantially as herein described and shown, characterized particularly by the bright and unique multicolored pigmentation of the flowers, the flower coloration being confined within the orange-red and yellow range.

No references cited.